United States Patent [19]

Ranford

[11] Patent Number: 5,279,549
[45] Date of Patent: Jan. 18, 1994

[54] CLOSED VENTILATION AND SUCTION CATHETER SYSTEM

[75] Inventor: Alan B. Ranford, St. Louis, Mo.

[73] Assignee: Sherwood Medical Company, St. Louis, Mo.

[21] Appl. No.: 960,225

[22] Filed: Oct. 13, 1992

Related U.S. Application Data

[63] Continuation of Ser. No. 638,239, Jan. 4, 1991, abandoned.

[51] Int. Cl.$^5$ .................... A61M 1/00; A61M 5/178; A61M 3/00; A61M 31/00
[52] U.S. Cl. ........................................ 604/34; 604/35; 604/36; 604/43; 604/45; 604/54; 604/118; 604/163; 604/171; 604/172; 604/250; 604/263; 604/266; 604/267; 604/902; 137/382; 137/384.2; 137/637; 251/4; 251/90
[58] Field of Search ................ 604/24, 27, 28, 30, 604/32–; 128/207.14–; 137/377, 382, 382.5, 383–; 251/637, 4–

[56] References Cited

U.S. PATENT DOCUMENTS

| | | | |
|---|---|---|---|
| 2,756,740 | 7/1956 | Deane | 128/1 |
| 3,208,145 | 9/1965 | Turner | 32/33 |
| 3,232,578 | 2/1966 | Cousins | 251/302 |
| 3,730,179 | 5/1973 | Williams | 128/207.14 |
| 3,871,358 | 3/1975 | Fukuda et al. | 128/2 M |
| 3,889,675 | 6/1975 | Stewart | 604/34 |
| 3,902,500 | 9/1975 | Dryden | 128/351 |
| 3,982,546 | 9/1976 | Friend | 128/350 R |
| 3,991,762 | 11/1976 | Radford | 128/276 |
| 4,061,142 | 12/1977 | Tuttle | 604/34 |
| 4,193,406 | 3/1980 | Jinotti | 128/204.18 |
| 4,235,232 | 11/1980 | Spaven et al. | 128/214.4 |
| 4,240,417 | 12/1980 | Holever | 604/207.14 |
| 4,256,099 | 3/1981 | Dryden | 128/207.15 |
| 4,300,550 | 11/1981 | Gandi et al. | 128/207.18 |
| 4,351,328 | 9/1982 | Bodai | 128/202.16 |
| 4,475,548 | 10/1984 | Muto | 128/207.14 |
| 4,524,802 | 6/1985 | Lawrence | 604/250 |
| 4,558,708 | 12/1985 | Labuda et al. | 128/719 |
| 4,563,176 | 1/1986 | Gustavsson et al. | 604/163 |
| 4,569,344 | 2/1986 | Palmer | 128/207.16 |
| 4,595,005 | 6/1986 | Jinotti | 128/205.24 |

(List continued on next page.)

OTHER PUBLICATIONS

"Trach Care New Closed Tracheal Suction System", Ballard Medical Products, Aug. 1985.
Concord/Portex, "Medical Products Catalog" 1989/90, front page, p. 66, and back page.

Primary Examiner—Randall L. Green
Assistant Examiner—K. M. Reichie
Attorney, Agent, or Firm—Andrew J. Beck; Montgomery W. Smith; Gene B. Kartchner

[57] ABSTRACT

A closed ventilation and suction catheter system for aspirating or suctioning the bronchial tree or trachea of a patient including a dual lumen catheter, the proximal end of the catheter is connected to a dual valve assembly which is connected to separate irrigation fluid and suction pressure sources and the distal end of the catheter is adapted to be slidably positioned in communication with the bronchial tree of a patient. A transparent and flexible envelope surrounds the catheter to protect the catheter from direct exposure to the atmosphere. The catheter is slidable from the inside of the envelope through an adaptor and a tracheal tube to communicate with the bronchial tree or trachea of the patient. A ventilator is connected to the adaptor near the distal end of the catheter to provide for the artificial ventilation of the patient. The bronchial tree or trachea of the patient may be irrigated and aspirated through the dual lumen catheter and the catheter may be substantially withdrawn into the envelope so that the distal end of the catheter system may be substantially positioned in an irrigation chamber in the adaptor so that the outer surface of the catheter may be flushed with irrigation fluid to remove any mucous accumulated on the distal end thereof.

3 Claims, 3 Drawing Sheets

U.S. PATENT DOCUMENTS

| | | | |
|---|---|---|---|
| 4,617,013 | 10/1986 | Betz | 604/39 |
| 4,638,539 | 1/1987 | Palmer | 29/157 R |
| 4,691,702 | 9/1987 | Chantzis | 128/207.16 |
| 4,696,296 | 9/1987 | Palmer | 128/207.16 |
| 4,696,669 | 9/1987 | Menhusen | 604/35 |
| 4,705,073 | 11/1987 | Beck | 137/625.25 |
| 4,708,717 | 11/1987 | Deane et al. | 604/35 |
| 4,762,125 | 8/1988 | Leiman et al. | 128/207.15 |
| 4,784,637 | 11/1988 | Ryder et al. | 604/32 |
| 4,805,611 | 2/1989 | Hodgkins | 128/207.14 |
| 4,834,726 | 5/1989 | Lambert | 604/281 |
| 4,836,199 | 6/1989 | Palmer | 128/207.16 |
| 4,838,255 | 6/1989 | Lambert | 128/202.16 |
| 4,850,350 | 7/1989 | Jackson | 604/33 |
| 4,852,551 | 8/1989 | Opie et al. | 604/34 |
| 4,872,579 | 10/1989 | Palmer | 128/205.19 |
| 4,938,741 | 7/1990 | Lambert | 604/19 |
| 4,955,375 | 9/1990 | Martinez | 128/207.15 |
| 4,967,743 | 11/1990 | Lambert | 128/207.16 |
| 5,025,806 | 6/1991 | Palmer et al. | 128/207.14 |
| 5,029,580 | 7/1991 | Radford et al. | 128/207.14 |
| 5,060,646 | 10/1991 | Page | 128/207.14 |
| 5,065,754 | 11/1991 | Jensen | 128/207.14 |
| 5,083,561 | 1/1992 | Russon | 604/119 |
| 5,125,893 | 6/1992 | Dryden | 604/171 |
| 5,133,345 | 7/1992 | Lambert | 604/171 |
| 5,134,996 | 8/1992 | Bell | 604/171 |
| 5,135,490 | 8/1992 | Strickland | 604/48 |
| 5,139,018 | 8/1992 | Brodsky et al. | 128/207.16 |
| 5,140,983 | 8/1992 | Jinotti | 604/267 |
| 5,156,186 | 10/1992 | Manska | 137/385 |
| 5,165,420 | 11/1992 | Strickland | 604/28 |
| 5,167,622 | 1/1992 | Muto | 604/35 |
| 5,181,908 | 1/1993 | Bell | 604/28 |

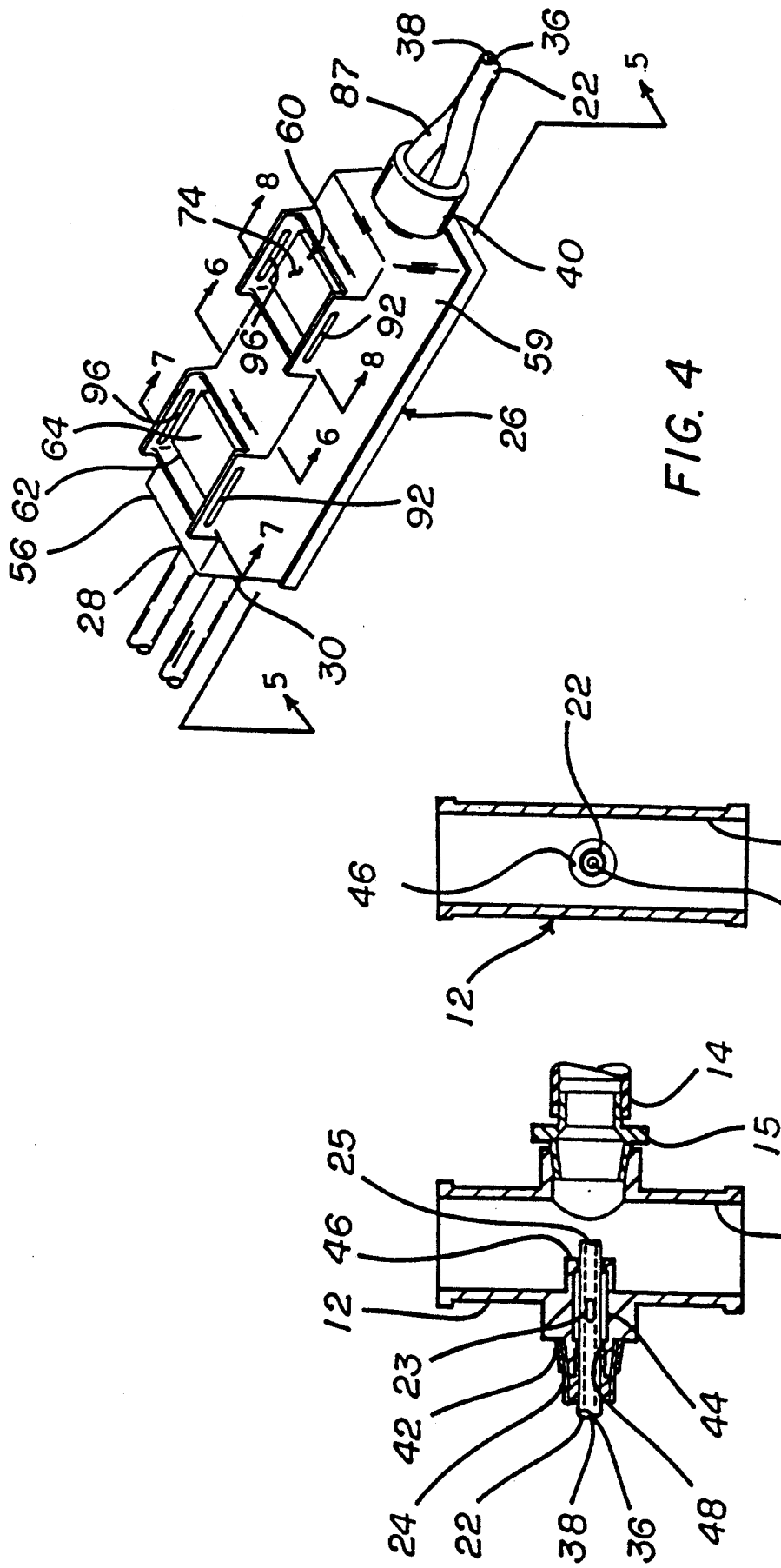

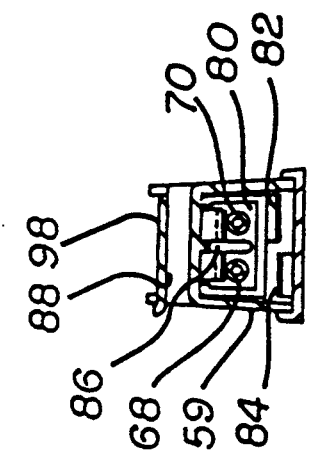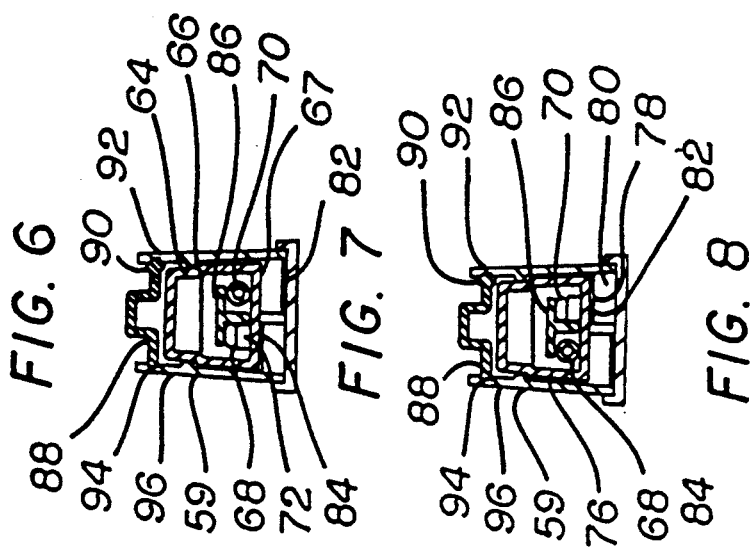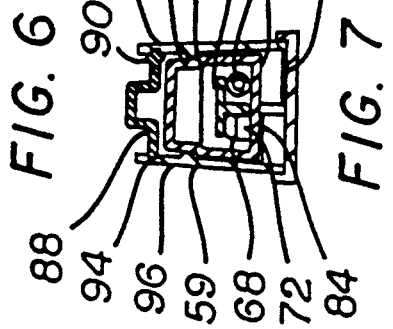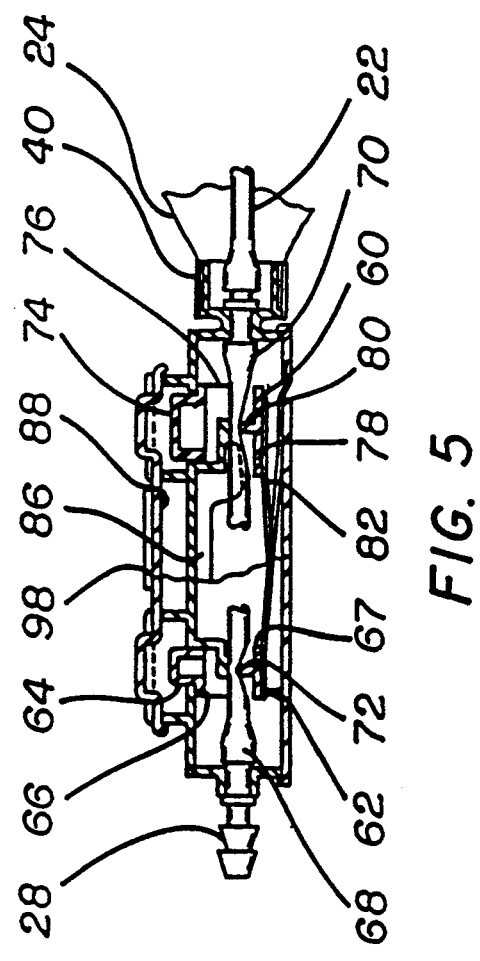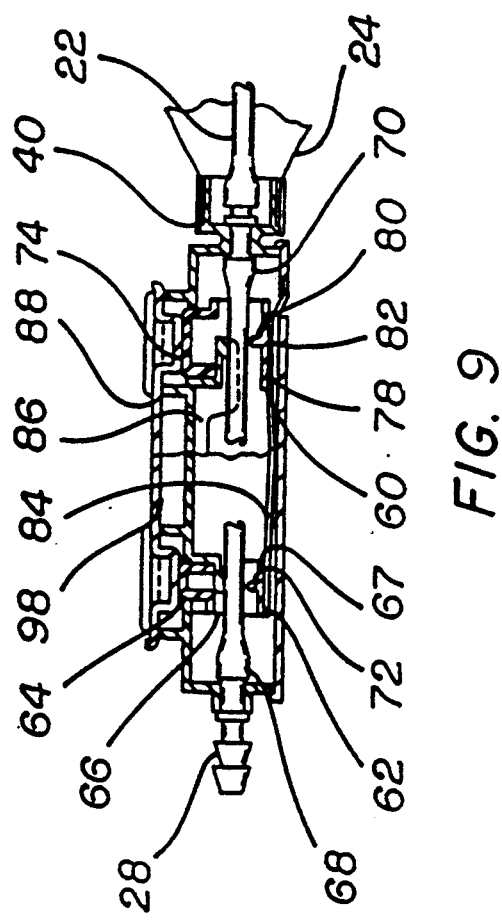

CLOSED VENTILATION AND SUCTION CATHETER SYSTEM

This is a continuation of copending application(s) Ser. No. 07/638,239 filed on Jan. 4, 1991, now abandoned.

FIELD OF THE INVENTION

The present invention is related to a tracheal ventilation and suction catheter system, more particularly to a closed system suction catheter suitable for use with a ventilation apparatus to remove mucous from the bronchial tree in the lungs of a patient and to remove the mucous which is deposited on the suction catheter during aspiration of the patient to facilitate the repetitive use of the suction catheter.

BACKGROUND OF THE INVENTION

A variety of systems for ventilating and aspirating secretions from the bronchial tree in the lungs of a patient have been proposed and are in use. One form of the currently available systems include a ventilator or respirator adapted to provide a flow of oxygenated air to a patient through a T-shaped tracheal tube adaptor which incorporates a port through which a separate single use suction catheter for the intermittent suctioning of mucous from the bronchial tree of a patient can be inserted. Although these systems have proven to be satisfactory for the ventilation of a patient, one major disadvantage in using these systems is that the aspiration of mucous from the patient requires the opening of the ventilation system and interruption of the ventilation process while a suction catheter is inserted into the patient's trachea. The act of interrupting the ventilation of a critically ill patient and then actually suctioning or aspirating air from their respiratory system for approximately 20 seconds may have a very deleterious effect on the patient. During the aspiration process, the alveolar gases in the lungs of the patient will also be removed in addition to the mucous. The loss of alveolar gases may result in hypoxia which may then cause further complications in the patient such as arrythmia or tachycardia. Because the hypoxia may continue in the patient for up to one hour, it is usually necessary to hyperoxygenate the patient before and after the aspiration to counter the oxygen deficit experienced during aspiration.

The aspiration of a patient's bronchial tree is usually required to be performed a number of times throughout a twenty-four hour period and therefore, numerous suction catheters are used in a twenty-four hour period with this type of catheter system. It is therefore desirable to provide a catheter system wherein the ventilation of the patient may be continued during aspiration and wherein the suction catheter is reusable.

In more recent times, the use of closed ventilation and suction catheter systems have been suggested to simultaneously ventilate and suction the bronchial tree or trachea of a patient. Some examples of such closed ventilation and suction catheter systems are disclosed in U.S. Pat. Nos. 3,991,762, 4,569,344, 4,638,539, 4,805,611, 4,834,726, 4,696,296 and 4,836,199. The use of these closed ventilation and suction catheter systems is a departure from the prior practice of opening the ventilation system and using a fresh suction catheter for each aspiration process. The above-identified closed ventilation and suction catheter systems provide a reusable suction catheter which is surrounded by a transparent envelope and which may be used without disconnecting the patient from the ventilator. One of the major advantages of this type of system is that the user may manipulate the catheter through the envelope without directly contacting the catheter either prior to or after insertion into the patient.

During the aspiration procedure, it is sometimes necessary to irrigate the upper bronchial tree or trachea of the patient to help break up thick accumulations of mucous in the patient. This is typically done by injecting a saline solution into the patient's airway through the T-shaped tracheal tube adaptor. The saline solution then drains down the patient's airway and is removed with the mucous through the suction catheter.

In a recently marketed closed ventilation and suction catheter system marketed by Concord/Portex of Keene, New Hampshire, USA, a dual lumen suction catheter is provided which includes an irrigation inlet port on the proximal end of the catheter. The irrigation inlet port includes a luer fitting thereon so that irrigation fluid may be supplied to the secondary lumen using either a syringe or a fluid filled capsule. The secondary lumen of this suction catheter opens approximately 1 centimeter from the distal end of the suction catheter. The proximal end of this catheter includes a single valve in communication with the primary lumen of the catheter and the secondary lumen is unobstructed between the proximal and distal ends of the catheter.

SUMMARY OF THE INVENTION

Therefore, it is an object of the present invention to provide an improved closed ventilation and suction catheter system for ventilating and aspirating the bronchial tree or trachea of a patient during suctioning which allows for the continuous ventilation of the patient and provides a reusable dual lumen suction catheter.

It is also an object of the present invention to provide a dual valve member or assembly to control the flow of irrigation fluid and suction pressure to the bronchial tree or trachea of a patient through the dual lumen catheter.

It is yet another object of the present invention to provide a catheter system which allows the distal end of the catheter to be separately flushed with fluid to remove any excess mucous which may have accumulated therein or thereon during aspiration of the patient after removal of the catheter from the bronchial tree or trachea of the patient.

In accordance with the principles of the present invention, a closed ventilation and suction catheter system is provided which allows for the irrigation and aspiration of the bronchial tree or trachea of the patient through a suction catheter while maintaining ventilation to the patient. The preferred form of the catheter system includes a dual lumen catheter having primary and secondary lumens with proximal and distal ends. The proximal end of the primary lumen is connected to a valve member which is in communication with a source of suction pressure such as a hospital wall suction unit. The proximal end of the secondary lumen is separately connected to the valve member and is in flow communication with either a continuous source, a syringe or a sealed capsule of irrigation fluid. The distal end of the dual lumen catheter is slidable through a reduced diameter irrigation chamber in the tracheal tube adaptor to communicate with the bronchial tree or trachea of a patient. A transparent and flexible envelope loosely surrounds the dual lumen catheter when the catheter is removed from the bronchial tree or trachea of the patient to protect the dual lumen catheter from exposure to the atmosphere.

The tracheal tube adaptor allows the catheter to slide through the tracheal tube adaptor to communicate with the bronchial tree or trachea of the patient. A ventilator is positioned in communication with the tracheal tube adaptor on the distal end of the catheter system to provide continuous ventilation to the patient. A pair of reduced diameter members are provided in the proximal portion of the tracheal tube adaptor to effectively obstruct the flow of air between the adaptor and the distal end of the envelope. The dual lumen catheter allows the user to flush the outer surface of the distal portion of the catheter with fluid after the catheter has been removed from the patient so that any mucous accumulated on the distal end of the catheter during aspiration of the patient is removed therefrom by flushing the distal end of the catheter while simultaneously or sequentially applying suction pressure therethrough when the distal end of the catheter is positioned adjacent to the irrigation chamber.

In accordance with another aspect of the present invention, a dual valve assembly is provided to allow for the controlled application of suction pressure and irrigation fluid to the bronchial tree or trachea of the patient through the suction catheter. The distal end of the dual valve assembly is attached to the proximal end of the dual lumen catheter and the proximal end of the dual valve assembly is connected to a source of irrigation fluid and a source of suction pressure.

In accordance with another aspect of the present invention, a method is provided for aspirating the bronchial tree or trachea of a patient with a closed ventilation and suction catheter system comprising the steps of providing a valve means for controlling the continuous and/or alternating aspiration and irrigation of the bronchial tree or trachea of the patient through the catheter. The catheter assembly of the present invention allows for the controlled irrigation and aspiration of the bronchial tree or trachea of the patient by providing a proximally positioned dual valve assembly to manually regulate the flow of irrigation fluid and suction pressure applied to the patient through the catheter. By positioning the dual valve assembly on the proximal end of the catheter, the user may conveniently operate the valve members while the catheter is positioned in the bronchial tree or trachea of the patent or when the distal end of the catheter is withdrawn into the tracheal tube adaptor.

These and other objects and advantages of the present invention will become apparent from the following detailed description of the preferred embodiment and the drawings.

BRIEF DESCRIPTION OF THE DRAWINGS

FIG. 2 is a cross-sectional view of the distal end of the catheter assembly and tracheal tube adaptor as shown in FIG. 1 and taken generally along line 2—2 of FIG. 1;

FIG. 3 is a cross-sectional view of the distal end of the catheter assembly and tracheal tube adaptor as shown in FIG. 4 is an enlarged perspective view of the dual valve assembly of the present invention as shown in FIG. 1;

FIG. 5 is a cross-sectional view of the dual valve assembly as shown in FIG. 4 and taken generally along line 5—5 of FIG. 4 showing the reversible cover installed thereon in a position to maintain the irrigation and suction valve members in the closed position and showing the irrigation tubing on the left side of the figure and the suction tubing on the right side of the figure;

FIG. 6 is a cross-sectional view of the dual valve assembly as shown in FIG. 4 and taken generally along line 6—6 of FIG. 4 showing the suction tubing and irrigation tubing of the dual valve assembly;

FIG. 7 is a cross-sectional view of the dual valve assembly of the present invention taken generally along line 7—7 of FIG. 4 with the reversible cover installed thereon and showing the irrigation valve member of the present invention in the closed position;

FIG. 8 is a cross-sectional view of the dual valve assembly of the present invention taken generally along line 8—8 of FIG. 4 with the reversible cover installed thereon and showing the suction valve member of the present invention in the closed position; and FIG. 9 is a side view partially in cross-section, of the dual valve assembly as shown in FIG. 4 and taken generally along lines 5—5 of FIG. 4 showing the reversible cover installed thereon in a position to maintain the irrigation and suction valve members in the open position and showing the irrigation tubing on the left side of the figure and the suction tubing on the right side of the figure.

DETAILED DESCRIPTION OF THE INVENTION

Figure 1:
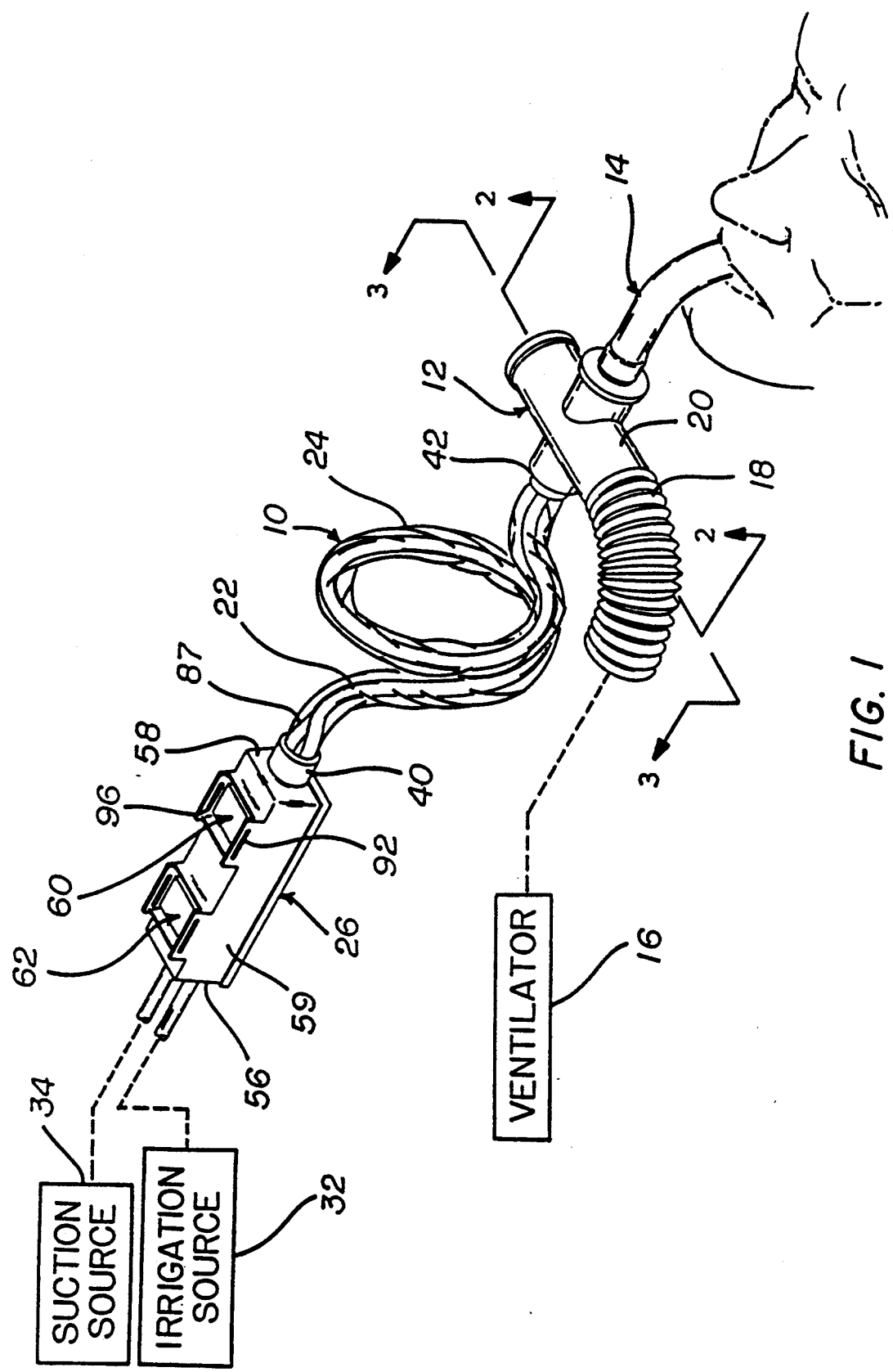
FIG. 1 is a perspective view of a closed ventilation and suction catheter system according to the present invention.

In describing the present invention, the "proximal end" of a part refers to the end of the part closest to the user or health care worker. The "distal end" of a part refers to the end of the part closest to the patient.

Referring to FIG. 1 of the drawings, a closed ventilation and suction catheter assembly is shown and generally referred to herein as catheter assembly 10. The catheter assembly 10 is adapted to be placed in communication with the bronchial tree or trachea of a patient via a conventional tracheal tube 14. The distal end of the catheter assembly 10 includes a generally T-shaped tracheal tube adaptor 12 which is adapted to be connected to the tracheal tube 14 and a ventilator 16 via a flexible tubing member 18 through a side opening 20 near the proximal end of the adaptor 12.

The catheter assembly 10 of the preferred embodiment of the present invention generally includes a dual lumen catheter 22 with proximal and distal ends. The catheter 22 is protected within a transparent and flexible envelope 24 and includes an irrigation outlet port 23 and a suction inlet port 25 near the distal end thereof as illustrated in FIG. 2. The proximal end of the catheter 22 and the proximal end of the envelope 24 are fixedly connected to a dual valve assembly 26. The proximal end of the dual valve assembly 26 includes separate irrigation and suction ports, 28 and 30, respectively thereon. The irrigation and suction ports, 28 and 30, respectively, are connected in flow communication with irrigation and suction sources 32 and 34, respectively as described more fully hereinafter.

The catheter 22 of the catheter assembly 10 is an elongated tubular member having a primary lumen 36 for the passage of suction pressure therethrough and a secondary lumen 38 for the passage of irrigation fluid therethrough. The catheter 22 is adapted to slide within the envelope 24 so that the distal end of the catheter 22 is movable from an initial location near the adaptor 12 on the distal end of the catheter assembly 10 to a second location wherein the distal end of the catheter 22 extends into the bronchial tree or trachea of the patient. A first collar 40 fixedly attaches the proximal end of the envelope 24 to the distal end of the dual valve assembly 26. A second collar 42 fixedly attaches the distal end of the envelope 24 to the proximal end of the adaptor 12. The envelope 24 surrounds substantially the entire length of the catheter 22 when the catheter 22 is not in use to protect the catheter 22 from exposure to the atmosphere and to allow the user to manipulate the catheter 22 in the envelope 24 without directly contacting the catheter 22. The catheter assembly 10 is designed so that the catheter 22 slides freely inside the envelope 24; through the adaptor 12 and tracheal tube 14 to allow communication between the distal end of the catheter 22 and the bronchial tree or trachea of the patient without adversely affecting ventilation of the patient.

The adaptor 12 at the distal end of the catheter assembly 10 is best illustrated in FIGS. 2 and 3 and includes a pair of side openings 20 therein to provide a continuous source of ventilation therethrough for the patient. The distal side of the adaptor 12 is removably mounted to the proximal end of the tracheal tube 14 by a standard connector which slidably fits inside the proximal end of the tracheal tube 14 and inside the distal end of the adaptor 12. The proximal side of the adaptor 12 includes an irrigation chamber 44 which is formed between a distal reduced diameter member 46 and a proximal reduced diameter member 48. The diameter of the distal member 46 is larger than the diameter of the proximal member 48 and the diameter of both members 46 and 48 are slightly larger than the outer diameter of the catheter 22 so that the catheter 22 may slide therethrough. The diameter of the proximal member 48 is also chosen to minimize the flow of air between the envelope 24 and adaptor 12 so that the operation of the ventilator is not adversely affected by the present invention.

As illustrated in FIGS. 4–10, the dual valve assembly 26 of the present invention 26 includes proximal and distal ends 56 and 58, respectively, and housing 59. As described previously, a first collar 40 is fixedly mounted at the distal end of the dual valve assembly 26 to attach the envelope 24 and proximal end of the catheter 22 to the dual valve assembly 26. The irrigation and suction ports, 28 and 30, respectively, are provided at the proximal end 56 of the dual valve assembly 26 to connect a source of irrigation fluid 32 to the irrigation port 28 and to connect the suction source 34 to the suction port 30.

As illustrated in FIGS. 5 and 9, the dual valve assembly 26 includes a suction valve member 60 to allow for the manual control of the suctioning of aspirated fluids from the bronchial tree or trachea of the patient through the primary lumen 36 of the catheter 22 and an irrigation valve member 62 to allow for the manual control of the flow of irrigation fluid through the secondary lumen 38 of the catheter 22. As shown in FIGS. 5 and 7, the irrigation valve member 62 is movably positioned in the housing 59 of the dual valve assembly 26 and has a generally rectangularly shaped cross section. A finger member 64 extends upwardly through an opening in the top surface of the housing to allow the user to manually actuate the irrigation valve member 62. A pair of sidewalls 66 extend downwardly from the finger member to a horizontally oriented lower portion 67 so that both the irrigation tubing 68 and the suction tubing 70 are encircled by the irrigation valve member 62. A tab member 72 is aligned with the irrigation tubing 68 and extends upwardly from the lower portion 67 of the irrigation valve member 62 to selectively close the irrigation tubing as described more fully hereinafter.

As illustrated in FIG. 8, the suction valve member 60 is movably positioned in the housing 59 of the dual valve assembly 26 and has a generally rectangularly shaped cross section. As with the irrigation valve member 62, the suction valve member 60 includes a finger member 74: a pair of sidewalls 76: a horizontally oriented lower portion 78 and an upwardly extending tab member 80. As illustrated in FIGS. 1 and 4, the suction valve member 60 is positioned distally of the irrigation valve member 62 and the finger member 74 on the suction valve member 60 is larger than the finger member 64 on the irrigation valve member 62. The suction and irrigation valve members, 60 and 62, are mounted along the proximal end of the catheter assembly 10 to allow the user to conveniently control the flow of irrigation fluid and suction pressure through the catheter 22 whether the distal end of the catheter 22 is in the bronchial tree or trachea of the patient or in the adaptor 12 of the catheter assembly 10 as described hereinafter. The suction and irrigation valve members, 60 and 62, of the present invention, are able to operate simultaneously, independently, or in combination to provide the desired amount of suction pressure and irrigation fluid to the bronchial tree or trachea of the patient.

As illustrated in FIGS. 5 and 9, the movement of the suction valve member 60 is controlled by a resilient first spring member 82 which contacts the lower portion 78 of the suction valve member 60 and biases the suction valve member 60 to a closed position (FIG. 8). A separate resilient second spring member 84 contacts the lower portion 67 of the irrigation valve member 62 and rises the irrigation valve member 62 to the closed position as shown in FIGS. 5 and 7. The two spring members 82 and 84 are engagably mounted along the lower portion, 67 and 78, of each valve member, 60 and 62. The spring members 82 and 84 bias the valve members, 60 and 62, in the closed position wherein the irrigation tubing 68 and/or suction tubing 70 is pinched closed between the upwardly extending tab members, 80 and 72, and an elongate platform member 86. The platform member 86 is oriented generally longitudinally in the dual valve assembly 26 and is fixedly mounted along the inner surface of the housing 59 (FIGS. 5 and 9). The irrigation and suction tubing, 68 and 70, in the dual valve assembly 26 extend in a side-by-side relationship in the housing 59 to communicate with the irrigation inlet port 28 and the suction inlet port 30 on the proximal end 56 of the dual valve assembly 26. The suction tubing 70 extends to the distal end 58 of the dual valve control assembly 26 to communicate with the primary lumen 36 of the catheter 22. The irrigation tubing 68 extends to the distal end 5 of the dual valve control assembly 26 to communicate with the secondary lumen 38 of the catheter through a relatively short bypass tube 87.

As described briefly above, the catheter tube 22 is preferably a dual lumen catheter comprised of a primary lumen 36 and a secondary lumen 38. When the distal end of the catheter 22 is positioned in the bronchial tree or trachea of the patient, the secondary lumen 38 is used to deliver irrigation fluid from the source of irrigation fluid 32 to the bronchial tree or trachea of the patient and the primary lumen 36 is used to deliver suction pressure from the source of suction 34 to the bronchial tree or trachea of the patient. The dual valve assembly 26 allows the health care worker to control the amount of irrigation fluid and/or suction pressure applied to the bronchial tree or trachea of the patient by depressing the appropriate valve member 60 or 62 to open the desired tubing 68 and 70 in the dual valve assembly 26. Because the outer diameter of the catheter 22 is smaller than the inner diameter of the adaptor 12 and the tracheal tube 14, the patient is continuously ventilated during the procedure except during the short period when suction is actually being applied to the patient.

A further use of the catheter system 10 of the present invention is to remove the mucous which will typically accumulate on the interior of the adaptor 12 as the catheter 22 is withdrawn from the bronchial tree or trachea of the patient. As briefly described above, the distal member 46 and the proximal member 48 are spaced apart on the proximal side of the adaptor 12 to form an irrigation chamber 44 therebetween. During aspiration of the patient, mucous will accumulate on the outer surface of the catheter 22. With the present invention, the proximal portion of the catheter 22 may be withdrawn into the envelope 24 so that the distal end of the catheter 22 is located adjacent to the distal side of the distal member 46. In this position, the irrigation outlet port 23 is positioned within the irrigation chamber 44 and the suction outlet port 28 is preferably positioned distally of the distal member 46. In order to remove the mucous from the distal portion of the catheter 22, the user may then direct a small amount of irrigation fluid through the irrigation outlet port 23 of the catheter 22 and into the irrigation chamber 44 to break up the mucous which has accumulated on the distal portion of the catheter. Simultaneously with the use of irrigation fluid, suction pressure is applied through the suction inlet port 25 to immediately draw the irrigation fluid and mucous from the from the irrigation chamber 44 and into the suction inlet port 25. The simultaneous operation of the suction valve member 60 and the irrigation valve member 62 is designed to cause minimal interruption to the ventilation of the patient as the mucous is removed from the distal portion of the catheter 22.

During sterilization and storage of the catheter system 10 of the present invention, the irrigation and suction tubing, 68 and 70, in the dual valve assembly 26, may become permanently deformed if the first and second spring members, 82 and 84, are allowed to pinch the irrigation and suction tubing, 68 and 70, in a closed position for an extended period of time. If the irrigation and suction tubing, 68 and 70, is permanently deformed by long intervals of pinching, the flow of irrigation fluid and suction therethrough is adversely effected and the patient may not be adequately aspirated. Therefore, as shown in FIGS. 5, 7 and 8, an additional feature of the present invention is to provide a reversible cover 88 on the dual valve control assembly 26 which engages and depresses the suction valve member 60 and the irrigation valve member 62 to maintain the valve members, 60 and 62, in an open position during extended periods of time. For example, it is preferable to maintain the valve members, 60 and 62, in an open position during sterilization, transport, storage or initial installation of the catheter 22. As shown in FIGS. 7 and 8, the reversible cover 88 includes a pair of first tab members 90 which releasably fit into a pair of slots 92 on the housing 59 and a pair of second tab members 94 which are releasably retained in a pair of detents 96 on the housing 59 of the dual valve assembly 26. As shown in FIG. 9, the inner surface 98 of the reversible cover 88 is sized to engage the top surface of the finger members, 64 and 74, of the valve members, 60 and 62, to maintain on lock the valve members, 60 and 62, in an open position to prevent the valve members, 60 and 62, from pinching or deforming the irrigation and suction tubing 68 and 70. When the reversible cover 88 has been installed on the housing 59 of the dual valve assembly 26, the valve members, 60 and 62, are prevented from moving to any other position until the reversible cover 88 has been removed.

A secondary function of the reversible cover 88 is to prevent the valve members 60 and 62 from being inadvertently depressed during incubation or between aspiration procedures. As illustrated in FIGS. 5–8, the reversible cover 88 may be installed on the housing 59 of the dual valve assembly 26 so that the inner surface 98 of the reversible cover 88 extends upwardly from the from the top of the dual valve assembly 26. In this position, the reversible cover 88 prevents on locks the valve members, 60 and 62, from being inadvertently depressed so that the irrigation and suction tubing, 68 and 70, remain closed during intubation or between aspiration procedures. As illustrated in FIGS. 7 and 8, the reversible cover 88 is retained in this reversed position by inserting the first tab members 90 into the slots 92 and inserting the second tab members 94 into the detents 96 on the housing 59.

The catheter 22 in the catheter assembly 10 of the present invention can be readily inserted into the patient and withdrawn from the patient without direct exposure of the catheter 22 to the environment and the catheter 22 may be reused on the same patient for an extended period of time. The catheter 22 of the present invention and the individual components associated therewith such as the envelope 24, the adaptor 12, tracheal tube 14, and the dual valve assembly 26 may be used for extended periods of time with any of these components being readily disposable and/or replaceable as needed.

While the preferred embodiment of the invention has been illustrated and described above, it will be appreciated that various changes may be made therein without departing from the spirit and scope of the present invention which is defined by the following claims.

What is claimed is:

1. A catheter assembly for the irrigation and suctioning of the lungs of a patient, said catheter assembly comprising;
   a catheter including an elongated tubular member having a plurality of lumens extending therethrough, said tubular member having proximal and distal ends thereon;
   a valve assembly having a plurality of valve members therein wherein said valve assembly is operatively associated with said proximal end of said catheter and in operative flow communication with said lumens of said catheter to selectively enable and disable the irrigation and suctioning of the lungs of the patient through said lumens of said catheter;

adaptor means operatively associated with said catheter to enable said distal end of said catheter to be inserted into the lungs of the patient therethrough;

said distal end of said catheter including at least one opening from one of said lumens adjacent thereto to enable communication with the lungs of the patient through said catheter; and envelope means operatively associated with said valve assembly and said adaptor means for selectively sealing said catheter from exposure to the atmosphere;

wherein said valve assembly further including a first valve member movable between an open and a closed position to operatively control the flow of irrigation fluid through one of said lumens in said catheter and a second valve member movable independently of said first valve member between an open and a closed position to operatively control the flow of suction pressure through another of said lumens in said catheter, said first valve member movable independently of said second valve member; and means for reversible mountings on said valve assembly in association with said first and second valve members to selectively lock said first and second valve members in either said open position or said closed position concurrently, wherein said reversible mounting means is a cover.

2. The catheter assembly in accordance with claim 1 wherein said cover is mountable in a first position on said valve assembly wherein said first and second valve members are maintained in said open position by contact with said cover to enable the flow of irrigation fluid and suction pressure through said lumens of said catheter.

3. The catheter assembly in accordance with claim 1 wherein said cover is mountable in a second position on said valve assembly wherein said first and second valve members are maintained in said closed position to prevent the flow of irrigation fluid and suction pressure through said lumens of said catheter.

* * * * *